United States Patent [19]

Gallo-Torres et al.

[11] 4,310,543

[45] Jan. 12, 1982

[54] PROSTAGLANDIN COMPOSITIONS

[75] Inventors: Hugo E. Gallo-Torres, Livingston; Navnit H. Shah, Clifton, both of N.J.

[73] Assignee: Hoffmann-La Roche Inc., Nutley, N.J.

[21] Appl. No.: 195,575

[22] Filed: Oct. 9, 1980

[51] Int. Cl.$^3$ .................. A61K 31/215; A61K 31/19
[52] U.S. Cl. .................................. 424/305; 424/317
[58] Field of Search ............................... 424/305, 317

[56] References Cited

U.S. PATENT DOCUMENTS 4,052,446 10/1977 Holland et al. .................. 424/317

OTHER PUBLICATIONS

Hayasaki et al., Chem. Abst., vol. 81 (1974) p. 29,510Z.
Tsukada et al., Chem. Abst., vol. 90 (1979) p. 127,529T.

*Primary Examiner*—Sam Rosen
*Attorney, Agent, or Firm*—Jon S. Saxe; George M. Gould; John B. Wilson

[57] ABSTRACT

Orally administrable pharmaceutical compositions in the form of a soft gelatin capsule containing a prostaglandin and ascorbic acid or ascorbyl palmitate which are dissolved in polyethylene glycol or polyoxyethylene sorbitan esters of fatty acids or combinations thereof. The compositions are especially useful in improving bioavailability and stability of the prostaglandin in pharmaceutical dosage form.

24 Claims, No Drawings

PROSTAGLANDIN COMPOSITIONS

BACKGROUND OF THE INVENTION

Natural prostaglandins are potent inhibitors of basal as well as stimulated gastric acid production. A deficiency of prostaglandins of the E-type is involved in the pathogenesis of peptic ulcer disease. Generally prostaglandins have usefulness therapeutically, not only for their antisecretory activity, but for their antihypertensive activity and have been employed as cardiovascular agents and as agents for inducing labor in pregnancies and in terminating pregnancies.

A difficulty encountered in making prostaglandins therapeutically effective has been due to poor bioavailability as to their antisecretory activity in dosage form and their instability in the dosage form.

In particular attempts to stabilize dosage forms of prostaglandins have been reported in U.S. Pat. No. 3,826,823 which discloses dry preparations in which the prostaglandin is in a solid dispersion in polyvinylpyrrolidone at solid state; and U.S. Pat. No. 3,954,787 which discloses lyophilyzed pharmaceutical compositions containing prostaglandins, polyvinylpyrrolidone and succinic acid.

A number of the prostaglandins which may be incorporated in this invention as active ingredients have been disclosed in U.S. Pat. No. 4,052,446.

SUMMARY OF INVENTION

This invention provides prostaglandin compositions and a method for orally administrating the compositions. The compositions comprise a soft gelatin capsule that contains a mixture comprising a solvent selected from the group consisting of polyethylene glycol and polyoxyethylene sorbitan esters of fatty acids and combinations thereof, a therapeutically effective amount of a prostaglandin as an active ingredient, and a chemical effective amount of ascorbic acid or ascorbyl palmitate as a stabilizer. The prostaglandin compositions of this invention provide prostaglandins in a bioefficient dosage form having improved stability and bioavailability. The compositions of the invention are useful generally as antisecretory agents.

DETAILED DESCRIPTION OF THE INVENTION

The invention relates to orally administrable pharmaceutical compositions comprising a soft gelatin capsule. The capsule contains a mixture having an organic solvent which is effective in making any prostaglandin contained therein bioavailable in oral administration. The mixture in the capsule also has, as a active ingredient, a therapeutically effective amount of a prostaglandin. Furthermore the mixture in the capsule also has, as a stabilizer, a chemically effective amount of ascorbic acid or ascorbyl palmitate which is effective in stabilizing the prostaglandin.

The active ingredient is a prostaglandin of the general formula:

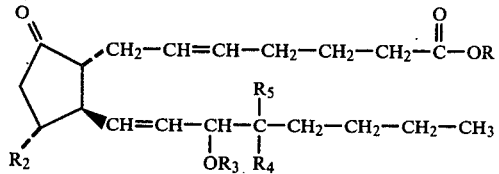

wherein R is hydrogen or lower alkyl; $R_2$ is hydrogen or lower alkyl; $R_3$ is hydrogen or acetyl; $R_4$ is hydrogen or lower alkyl; and $R_5$ is hydrogen, lower alkyl or fluoro.

The prostaglandins of the above general formula which are particularly suitable for the invention compositions are Nat-11R-methyl-16R-fluoro-15R-hydroxy-9-oxoprostacis-5-trans-13-dien-1-oic acid; Nat-11R,16,16-trimethyl-15R-hydroxy-9-oxoprosta-cis-5-trans-13-dien-1-oic acid; methyl-Nat-11R,16,16-trimethyl-15R-hydroxy-9-oxoprosta-cis-5-trans-13-dienoate; and (9R,11R,12S,15R,5Z,13E)-15-(acetyloxy)-11,16,16-trimethyl-9-oxoprosta-cis-5-trans-13-dien-1-oic acid.

The preferred concentration range for the prostaglandins is 0.025 to 2% by weight in the mixture (the solvent, the prostaglandin and ascorbyl palmitate) contained in the capsule comprising the invention, with the most preferred being 0.25 to 0.5%.

The term lower alkyl includes both straight-chain and branched-chain alkyl groups having from 1 to 7 carbon atoms, such as methyl, ethyl, and propyl, and the like. The term lower alkanoyl includes groups having from 1 to 7 carbon atoms such as methanoyl, ethanoyl, and the like.

The soft geletin capsule containing the mixture of solvent, active ingredient and stabilizer acts as a pharmaceutical carrier for the active ingredient in oral administration of the capsule. The capsules of the invention are preferably made of gelatin and maybe manufactured and prepared by conventional capsule-making equipment and procedures. For such procedures in particularly, reference is made to U.S. Pat. Nos. 2,899,361 and 2,928,128, which are herein incorporated by reference.

In the past it was generally believed that the bioavailability of prostaglandins in orally administrable form was achieved by dissolving the prostaglandin in solvents such as Tris-ethanol or phosphate buffers. In accordance with this invention it has been found surprisingly that polyoxyethylene sorbitan esters of fatty acids (PGSE) or polyethylene glycols (PEG) or combinations thereof are more effective and significant solvents than tris-ethanol or phosphate buffers in making the prostaglandin bioavailable. The improved bioavailability of the prostaglandins in turn improves the pharmacological effectiveness of the prostaglandins.

Particularly preferred PGSE are those wherein the esters are formed from aliphatic compounds having from 12 to 18 carbon atoms. The PGSE are polyoxyethylene polymers having 18–20 ethylene oxide groups where the sorbitan is esterified with a fatty acid such as stearic acid, oleic acid and palmitic acid. Among the preferred PGSE are Polysorbate 80 (polyethylene (20) sorbitan, mono-oleate) and Polysorbate 60 [polyoxyethylene (20) sorbitan mono-stearate]. The preferred polyethylene glycols are those of molecular weight range 200 to 6000; especially preferred are those with average molecular weight 400 (PEG-400) or 6000 (PEG-6000).

PGSE and PEG have been surprisingly found to be exceptionally suitable in increasing the bioavailability, potency and duration of the prostaglandin in oral administrations to animals (as illustrated in Example 10). The percentage of PEG or PGSE or combinations thereof by weight in the mixture contained by the capsule comprising the invention may vary from about 90.0 to 99.9%, with the preferred being about 97.0 to 99.5%.

The solvent of the invention may be of various combinations of polyoxyethylene sorbitan fatty acid esters or polyethylene glycols in any ratio which is liquid or which can be liquified by conventional warming methods.

The stabilizer for the prostaglandins of the invention is an ascorbate. The preferred ascorbate for the invention is ascorbic acid or ascorbyl palmitate. The preferred concentration range for the stabilizer is from about 0.05% to about 5% by weight of the mixture contained in the capsule comprising the invention, with the preferred being from about 0.2 to 2%. The foregoing range has been found to be a chemically effective amount for stabilizing the active ingredient. The chemical effect of the stabilizer has been found to be surprisingly effective in prolonging stability of the prostaglandins from a few weeks to several years.

Other stabilizers may be incorporated along with the ascorbate into the mixture contained in the capsule. Various compounds may be employed as these other stabilizers. Among the compounds which can act as these other stabilizers are included bisulfite, butylated hydroxyanisole (BHA), butylated hydroxy toluene (BHT), butylated hydroquinone, thiodipropionic acid, dilaurylthiodiprionate, ethoxyquine,$\alpha$-tocopherol, thiourea, thioglycerol, lecithin, propyl gallate, nor dihydroguairetic acid, 2 tert-butyl hydroquinone, and hydroquinone. The range of these other stabilizers can vary up to 0.5% by weight of the mixture contained in the capsule comprising the invention with the preferred being up to 0.2%.

The present invention also comprehends a method of orally administering the pharmaceutical compositions of the invention. In particularly the method comprises administering orally a soft gelatin capsule containing a mixture comprising a polyethylene glycol or a polyoxyethylene sorbitan ester of a fatty acid or combination thereof as a solvent, a therapeutically effective amount of a prostaglandin as an active ingredient and a chemically effective amount of ascorbic acid or ascorbyl palmitate as a stabilizer to provide effective bioavailability of the essential active ingredient and prolong stability of the active ingredient in dosage form.

The dosage amounts in which the prostaglandins as herein previously described are present in the mixture contained in the gelatin capsule as one dosage can vary as well as the number of dosages for each patient, depending on the requirements of the patients. The amounts can range from about 0.02 mg to about 10 mg daily in one or more dosages. Gelatin capsules containing a unit dosage of about 0.3 to about 2.5 mg of the active ingredient is the preferred amount.

A typical manner of making the invention compositions comprehends adding ascorbyl polymitate and butylated hydroxyanisole (BHA) to a liquid polyethylene glycol (PEG) at room temperature. If the PEG is not a liquid at room temperature, it may first be warmed until liquified. Thereafter the prostaglandin is added and mixed in the PEG mixture until dissolved. The process is preferably carried out under an atmosphere of nitrogen. The resulting mixture in liquid form is then used to fill soft gelatin capsules. The filling process as well as the making of the capsule itself are by any conventional methods well known in the art.

The present invention is further illustrated by the Examples which follow but are not intended to restrict the scope and spirit of the invention.

EXAMPLE 1

0.2 mg of butylated hydroxyanisole [BHA] and 1.0 mg of ascorbyl palmitate are added to and mixed conventionally until dissolved in 400 mg of polyethylene glycol-400 at room temperature under an atmosphere of nitrogen. To the resulting mixture is added 0.25 mg of Nat-11R,16,16-trimethyl-15R-hydroxy-9-oxoprosta-cis-5-trans-13-dien-1-oic acid [hereinafter referred to as trimethyl $PGE_2$ acid] at room temperature under nitrogen. The mixture is mixed conventionally under nitrogen until all added ingredients are dissolved. The resulting mixture in liquid form is thereafter filled into a soft gelatin capsule.

EXAMPLE 2

0.2 mg of BHA and 1.0 mg of ascorbic acid are added to and mixed until dissolved in a mixture of 200 mg of polyethylene glycol-200 and 200 mg of polysorbate-80 at room temperature under an atmosphere of nitrogen. To the resulting mixture is added 0.25 mg of trimethyl $PGE_2$ acid at room temperature under nitrogen. The mixture is thereafter mixed conventionally under nitrogen until all added ingredients are dissolved. The resulting mixture in liquid form is thereafter filled into a soft gelatin capsule.

EXAMPLE 3

300 mg of polyethylene glycol-400 and 100 mg of polyethylene glycol-4000 are mixed and warmed conventionally under nitrogen until the mixture is liquified. To the warmed-liquified mixture under nitrogen is added 0.1 mg BHA, 0.1 mg butylated hydroxytolune (BHT) and 1.0 mg of ascorbyl palmitate with conventional mixing until all ingredients are dissolved. Thereafter, while maintaining the liquid condition under nitrogen, 0.5 mg of trimethyl $PGE_2$ acid is added and dissolved with mixing. The liquid is then filled into a soft gelatin capsule.

EXAMPLE 4

0.2 mg of BHA, 0.2 mg of BHT and 1.0 mg ascorbyl palmitate are dissolved by conventional mixing in 400 mg of Polysorbate-80 at room temperature under nitrogen. To the resulting mixture under nitrogen is added 0.5 mg of trimethyl $PGE_2$ acid which is dissolved by mixing. The resulting liquid is then filled into a soft gelatin capsule.

EXAMPLE 5

A mixture of 200 mg each of Polysorbate-60 and Polysorbate-80 is warmed. To the resulting liquid mixture under nitrogen is added 0.2 mg BHA, 1.0 mg alpha-tocopherol and 2.0 mg ascorbyl palmitate and the mixture mixed until all ingredients are dissolved. Thereafter 0.25 mg of trimethyl $PGE_2$ acid is added under nitrogen and mixed conventionally until dissolved. The resulting mixture in the form of a liquid is filled into a soft gelatin capsule.

EXAMPLE 6

0.2 mg of 2-tert-butyl hydroquinon and 1.5 mg of ascorbic acid are dissolved in 200 mg of polyethylene glycol-400 with mixing under nitrogen conventionally at room temperature. Thereafter 0.25 mg of trimethyl $PGE_2$ acid is added and mixed until dissolved under nitrogen. The resulting liquid mixture is then filled into a soft gelatin capsule.

EXAMPLE 7

| | mg/capsule | | | |
|---|---|---|---|---|
| (8R,11R,12S,15R,5Z,13E)-acetyloxy 11,16,16-trimethyl-9-oxoprosta-5, 13-dien-1-oic acid (PG) | 0.25 | 0.1 | 0.50 | 1.0 |
| Polyethylene Glycol 400 (PEG 400) | 400 | 400.0 | 400.0 | 400.0 |
| Butylated Hydroxyanisole (BHA) | 0.2 | 0.2 | 0.2 | 0.2 |
| Ascorbyl Palmitate | 1.0 | 1.0 | 1.0 | 1.0 |

The above formulations were prepared utilizing the following procedure:

Dissolve BHA and ascorbyl palmitate in PEG 400. Add the active ingredient under an atmosphere of nitrogen. The resulting mixture in liquid form is filled into soft-shell gelatin capsules.

EXAMPLE 8

| | mg/capsule | | | |
|---|---|---|---|---|
| (8R,11R,12S,15R,5Z,13E)-acetyloxy 11,16,16-trimethyl-9-oxoprosta-5, 13-dien-1-oic acid | 0.025 | 1.0 | 0.50 | 1.0 |
| Polyethylene Glycol 400 | 200 | 200.0 | 200.0 | 200.0 |
| Polysorbate 80 | 0.2 | 0.2 | 0.2 | 0.2 |
| Butylated Hydroxyanisole | 1.0 | 1.0 | 1.0 | 1.0 |
| Ascorbyl Palmitate | | | | |

The above formulations were prepared utilizing the following procedure.

Dissolve BHA and ascorbyl palmitate in a mixture of PEG 400 and polysorbate 80. Add the active ingredient and dissolve under an atmosphere of nitrogen. The resulting mixture in liquid form is filled into soft-shell gelatin capsules.

EXAMPLE 9

11R,16,16,Trimethyl-15R-Hydroxy-9-oxoprosta-cis-5-trans-13-dienoic acid being tritiated in the hydrogen at position II (hereafter referred to as tritiated-PGE). The tritiated PGE was administered to rats in two different formulations designated I and II as shown in Table 1. Rats were prepared with catheter in the portal vein and a canulae in the stomach. The concentration of the tritiated PGE was adjusted to administer 10 μg/kg intragastrically in volume of 1 ml/rat. Portal vein blood samples (250 μl) were collected in heparinized tubes at specified times; 10 μl of plasma was dissolved in Aquasol scintillation fluid and counted in a scintillation counter. As shown in Table 2, the poorest absorption was observed with tritiated-PGE in Tris-Ethanol; while tritiated PGE in Polyethylene Glycol 400 showed the maximum absorption.

TABLE 1

Formulations I and II used in determining the bioavailability of tritiated-PGE in rats.

| Ingredients | Units | Formulation I | Formulation II |
|---|---|---|---|
| Tritiated-PGE | mcg | 2.5 | 2.5 |
| Polyethylene Glycol 400 | mg | 400.0 | — |
| BHA | mg | 0.2 | 0.2 |
| Tris | mg | — | 8 |
| Ethyl Alcohol q.s | ml | — | 1 ml |
| Water q.s. | ml | 1 ml | — |

TABLE 2

Bioavailability of tritiated-PGE in rats from Formulations I and II of Table 1.

| | Tritiated-PGE | |
|---|---|---|
| Formulation | Area under the curve (DPM × $10^4$) per 10 μl/m | Plasma Peak-level DPM × $10^4$ per 10μl of Plasma |
| I PEG 400 | 26.2 | 17 |
| II Tris-Ethanol mixture | 12.8 | 4.3 |

EXAMPLE 10

11R,16,16-trimethyl-15R-hydroxy-9-oxoprosta-cis-5-trans-13-dien-1-oic acid was put into dosage formulations designated as A, B and C in Table 3. Dogs prepared with Heidenhain Pouches were fasted overnight, during which time water was allowed ad libitum. Initially two basal samples of gastric juices were collected at 15 minute intervals, followed by IV infusion of histamine-HCl at submaximally stimulatory dose of 20 μg/kg/hr, with an infusion rate of 1 ml/minute. The various formulations were administered 90 minutes after the beginning of histamine-HCl infusion. The formulations were given orally. Samples of the gastric juices were collected at 15 minute intervals for 4 hours following administration of the formulations. The samples of gastric juices were assayed for pH, volume, total acid content (meq/ml) and total acid output. Tables 4 and 5 illustrate the percent inhibition of acid output (antisecretory effect) of the prostaglandin. As seen from Tables 4 and 5 the percent of acid output inhibition is surprisingly high for the formulation containing PEG and ascorbyl palmitate when compared to a placebo formulation (B) or to a formulation (C) not containing PEG.

TABLE 3

| Formulation Identification Type-Mixture | A Liquid | B Placebo mg/capsule | C Solid |
|---|---|---|---|
| tritiated-PGE | 0.25 | 0 | 0.25 |
| PEG-400 | 398.55 | 0 | 0 |
| Pluronic F-68* | 0 | 200.0 | 200.0 |
| Lactose (Anhydrous DTG) | 0 | 150.0 | 150.0 |
| Syloid 74** | 0 | 25.0 | 25.0 |
| Primojel*** | 0 | 50.0 | 50.0 |
| Cornstarch | 0 | 20.0 | 20.0 |
| Talc | 0 | 20.0 | 20.0 |
| BHA | 0.2 | 0.2 | 0.2 |
| Ascorbyl Palmitate | 1.0 | 1.0 | 1.0 |
| | 400.0 | 466.20 | 455.45 |

*Polyethylene-Polyxoypropylene co-polymer
**Silicone dioxide
***Modified Starch

TABLE 4

| Formulation Identification | A | B | C |
|---|---|---|---|
| Type-Mixture | Liquid | Placebo | Solid |
| μg of Prostaglandin per capsule | 250 | 0 | 250 |
| Minutes After Dosage Administration | ACID OUTPUT (% INHIBITION) | | |
| 15 | 53 | 0 | 0 |
| 30 | 62 | 0 | 0 |
| 45 | 94 | 0 | 0 |
| 60 | 67 | 4 | 0 |
| 75 | 95 | 7 | 1 |
| 90 | 87 | 0 | 10 |
| 105 | 89 | 0 | 28 |
| 120 | 81 | 2 | 0 |
| 135 | 65 | 6 | 15 |
| 150 | 70 | 12 | 0 |
| 165 | 69 | 1 | 0 |
| 180 | 61 | 18 | 0 |
| 195 | 48 | 21 | 0 |
| 210 | 47 | 4 | 0 |
| 225 | 39 | 0 | 15 |

TABLE 5

| Formulation Identification | A | B | C |
|---|---|---|---|
| Type-Mixture | Liquid | Placebo | Solid |
| μg of Prostaglandin per capsule | 250 | 0 | 250 |
| Minutes After Dosage Administration | VOLUME (% INHIBITION) | | |
| 15 | 10 | 0 | 0 |
| 30 | 61 | 1 | 0 |
| 45 | 91 | 1 | 0 |
| 60 | 83 | 0 | 0 |
| 75 | 81 | 1 | 0 |
| 90 | 77 | 1 | 0 |
| 105 | 80 | 0 | 17 |
| 120 | 72 | 9 | 0 |
| 135 | 58 | 4 | 12 |
| 150 | 49 | 6 | 0 |
| 165 | 40 | 0 | 0 |
| 180 | 44 | 0 | 0 |
| 195 | 11 | 0 | 0 |
| 210 | 14 | 0 | 0 |
| 225 | 59 | 0 | 1 |

EXAMPLE 11

Table 5 illustrates the surprising stability of 11R,16,16-trimethyl-15R-oxoprosta-9-cis-5-trans-13-dien-1-oic acid (0.5 or 0.25 mg/capsule) dissolved in PEG-400 in the presence of various stabilizers. Stability was determined at room temperature (RT) and at elevated temperatures in terms of the percent of degradation of the prostaglandin using conventionally a thin layer chromatographic method for analysis. The results indicates that the ascorbyl palmitate chemically stabilizes the prostaglandins in the PEG-400 formulation.

TABLE 6

| Stabilizer | Age | Degradation |
|---|---|---|
| None | 3 mo/RT | 2.0 |
| None | 3 mo/45° C. | 50.0 |
| BHA (0.5%) | 3 mo/RT | 2.0 |
| | 3 mo/45° C. | 50.0 |
| BHT (0.5%) | 3 mo/RT | 3–4 |
| | 3 mo/45° C. | 50.0 |
| Ascorbyl Palmitate (0.05%) | 3 mo/RT | 0.1 |
| | 3 mo/45° C. | 2.0 |
| BHA + Ascorbyl Palmitate (0.05%) each | 3 mo/RT | 0.2 |
| | 3 mo/45° C. | 3.0 |
| BHA + BHT 0.05% each | 5 days/RT | 0.2 |
| | 5 days/55° C. | 1.5 |
| 0.25% each | 5 days/RT | 0.3 |
| BHA + Ascorbyl Palmitate 0.05% each | 5 days/RT | 0.1 |
| | 5 days/55° C. | 0.2 |
| 0.25% each | 5 days/RT | 0.2 |
| BHA + alpha-tocopherol | 5 days/RT | 0.2 |
| 0.25% & 1% respectively | 5 days/55° C. | 3.0 |
| BHA + Ascorbic Acid | 5 days/RT | 0.2 |
| 0.25% each | 5 days/55° C. | 0.2 |
| BHA + BHA + alpha-tocopherol | 5 days/RT | 0.2 |
| | 5 days/55° C. | 3.0 |
| BHA + alpha-tocopherol + Propyl Gallate | 5 days/RT | 0.2 |
| | 5 days/55° C. | 3.4 |
| BHA + BHT + Ascorbyl Palmitate | 5 days/RT | 0.2 |
| | 5 days/55° C. | 0.2 |
| BHA + Ascorbyl Palmitate + alpha-tocopherol | 5 days/RT | 0.2 |
| | 5 days/55° C. | 0.2 |
| BHA + Ascorbyl Palmitate | 6 mos/RT | 0.1 |
| BHA + Ascorbyl Palmitate | 12 mos/RT | 0.1 |

We claim:

1. An orally administrable pharmaceutical composition comprising a soft gelatin capsule containing a mixture comprising a solvent selected from the group consisting of polyoxyethylene sorbitan esters of fatty acids, polyethylene glycols and combinations thereof; and as an active ingredient a therapeutically effective amount of a prostaglandin; and as a stabilizer a chemically effective amount of ascorbyl palmitate.

2. A composition according to claim 1 wherein the active ingredient is selected from compounds having the general formula:

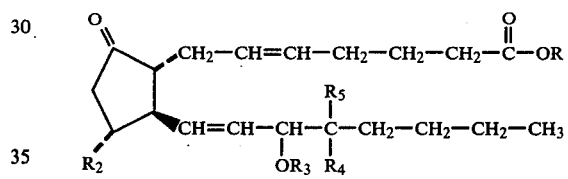

wherein R is hydrogen or lower alkyl; $R_2$ is hydrogen or lower alkyl; $R_3$ is hydrogen or acetyl; $R_4$ is hydrogen or lower alkyl; and $R_5$ is hydrogen, lower alkyl, or fluoro.

3. A composition according to claim 2 wherein the active ingredient is Nat-11R-methyl-16R-fluoro-15R-hydroxy-9-oxoprosta-cis-5-trans-13-dien-1-oic acid.

4. A composition according to claim 2 wherein the active ingredient is Nat-11R,16,16-trimethyl-15R-hydroxy-9-oxoprosta-cis-5-trans-13-dien-1-oic acid.

5. A composition according to claim 2 wherein the active ingredient is methyl-Nat-11R,16,16-trimethyl-15R-hydroxy-9-oxoprosta-cis-5-trans-13dienoate.

6. A composition according to claim 3 wherein the active ingredient is (8R,11R,12S,15R,5Z,13E)-15-(acetyloxy)-11,16,16-trimethyl-9-oxoprosta-cis-5-trans-13-dien-1-oic acid.

7. A composition according to claim 1 wherein the solvent is selected from polyethylene glycols having molecular weights from about 200 to about 6000.

8. A composition according to claim 7 wherein the polyethylene glycol has a molecular weight of about 400.

9. A composition according to claim 7 wherein the polyethylene glycol has molecular weight of about 6000.

10. A composition according to claim 1 wherein the polyoxyethylene sorbitan ester is selected from the group consisting of polyoxyethylene sorbitan stearate, polyoxythylene sorbitan oleate, and polyoxyethylene sorbitan palmitate.

11. A composition according to claim 1 wherein the solvent consists of polyethylene glycol-400 and polyethylene glycol-4000.

12. A composition according to claim 1 wherein the mixture further comprises a stabilizer selected from the group consisting of bisulfite, butylated hydroxyanisole, butylated hydroxytoluene, propyl gallate, nordihydroguairetic acid, 2-tert-butyl hydroquinone, thiodipropionic acid, dilaurylthio-dipropionate, ethoxyquin, alphatocopherol, thiourea, thioglycerol, lecithin and hydroquinone.

13. A method of orally administering a pharmaceutical composition, said method comprising administering a soft gelatin capsule containing a mixture comprising a solvent selected from the group consisting of polyoxyethylene sorbitan esters of fatty acids, polyethylene glycols and combinations thereof and as an active ingredient therapeutically effective amount of a prostaglandin; and as a stabilizer a chemically effective amount of ascorbyl palmitate.

14. A method according to claim 13 wherein the active ingredient is selected from compounds having the general formula:

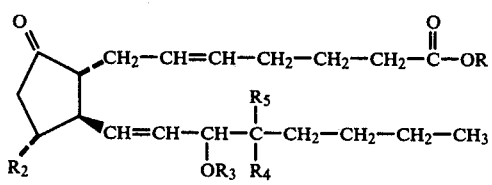

wherein R is hydrogen or lower alkyl; $R_2$ is hydrogen or lower alkyl; $R_3$ is hydrogen or acetyl; $R_4$ is hydrogen or lower alkyl; and $R_5$ is hydrogen, lower alkyl or fluoro.

15. A method according to claim 14 wherein the active ingredient is Nat-11R-methyl-16R-fluoro-15R-hydroxy-9-oxoprosta-cis-5-trans-13-dien-1-oic acid.

16. A method according to claim 14 wherein the active ingredient is Nat-11R,16,16-trimethyl-15R-hydroxy-9-oxoprosta-cis-5-trans-13-dien-1-oic acid.

17. A method according to claim 14 wherein the active ingredient is methyl-Nat-11R,16-16-trimethyl-15R-hydroxy-9-oxoprosta-cis-5-trans-13-dienoate.

18. A method according to claim 14 wherein the active ingredient is (8R,11R,12S,15R,5Z13E)-5-(acetyloxy)-11,16,16-trimethyl-9-oxoprosta-cis-5-trans-13-dien-1-oic acid.

19. A method according to claim 13 wherein the solvent is selected from polyethylene glycols having molecular weights from about 200 to about 6000.

20. A method according to claim 19 wherein the polyethylene glycol has molecular weight of about 400.

21. A method according to claim 19 wherein the polyethylene glycol has molecular weight of about 6000.

22. A method according to claim 13 wherein the polyoxyethylene sorbitan ester is selected from the group consisting of polyoxyethylene sorbitan sterate, polyoxyethylene sorbitan oleate, and polyoxyethylene sorbitan palmitate.

23. A method according to claim 13 wherein the solvent is selected from the group consisting of polyethylene glycol having a molecular unit of 400 and polyethylene glycol having a molecular unit of 4000.

24. A method according to claim 13 wherein the mixture further comprises a stabilizer selected from the group consisting of bisulfite, butylated hydroxyanisole, butylated hydroxytoluene, propylgallate, nordihydroguaiaretic acid, 2-tert-butyl hydroquinone, thiodipropionic acid, dilaurylthio-dipropionate, ethoxyguin, alphatocopherol, thiourea, thioglycerol, lecithin and hydroquinone.

* * * * *